(12) United States Patent
Ejlertsson

(10) Patent No.: US 7,622,286 B2
(45) Date of Patent: Nov. 24, 2009

(54) METHOD, A DEVICE AND AN ADDITIVE FOR DIGESTING ORGANIC MATTER

(75) Inventor: Jörgen Ejlertsson, Rimforsa (SE)

(73) Assignee: Tekiniska Verken I Linkoping AB, Linköping AB (SE)

( * ) Notice: Subject to any disclaimer, the term of this patent is extended or adjusted under 35 U.S.C. 154(b) by 420 days.

(21) Appl. No.: 11/604,828

(22) Filed: Nov. 28, 2006

(65) Prior Publication Data
US 2007/0184542 A1    Aug. 9, 2007

(30) Foreign Application Priority Data
Dec. 1, 2005    (SE) .................... 0502624

(51) Int. Cl.
*C12P 5/02* (2006.01)
(52) U.S. Cl. ...................... 435/167; 435/166
(58) Field of Classification Search .............. None
See application file for complete search history.

(56) References Cited

U.S. PATENT DOCUMENTS

| | | | |
|---|---|---|---|
| 4,315,823 A | 2/1982 | Witt et al. | |
| 4,529,701 A | 7/1985 | Seely | |
| 4,696,746 A | 9/1987 | Ghosh et al. | |
| 4,940,544 A | 7/1990 | Gode et al. | |
| 5,071,559 A | 12/1991 | Bleeker | |
| 5,228,995 A | 7/1993 | Stover | |
| 5,342,524 A | 8/1994 | Gaddy | |
| 5,413,713 A | 5/1995 | Day et al. | |
| 5,506,123 A * | 4/1996 | Chieffalo et al. | 439/139 |
| 5,783,081 A | 7/1998 | Gaddy | |
| 5,976,372 A * | 11/1999 | Vesterager | 210/603 |
| 6,254,775 B1 | 7/2001 | McElvaney | |
| 6,464,875 B1 | 10/2002 | Woodruff | |

FOREIGN PATENT DOCUMENTS

| | | |
|---|---|---|
| DE | 41 30 466 | 6/1992 |
| EP | 0332134 | 9/1989 |
| EP | O 531 954 | 3/1993 |
| EP | 0970922 | 1/2000 |
| EP | O 968 961 | 1/2000 |
| JP | 3000199 | 1/1991 |
| JP | 2004-025088 | 1/2004 |
| SE | 523 313 | 2/2005 |
| WO | WO 92/03393 | 3/1992 |
| WO | WO 02/37589 | 5/2002 |

OTHER PUBLICATIONS

Gilles Percheron et al. "Start-up of Anaerobic Digestion of Sulfate Wastewater." Bioresource Technology 61, 1997, pp. 21-27.
Johann Orlygsson et al. Anaerobic Degradation of Protein and the Role of Methane Formation in Steady State Thermophilic Enrichment Cultures, Pub Date 1993.
A. Jarvis et al. "Improvement of a Grass-Clover Silage-Fed Biogas Process by the Addition of Cobalt". Biomass and Bioenergy, vol. 12, No. 6, Apr. 1, 1997, pp. 453-460.
Paula L. Paulo, et al. "Effect of Cobalt on the Anaerobic Thermophilic Conversion of Methanol." Jan. 2, 2003, http://www.interscience.wiley.com. DOI: 10.1002/bit.10876.
Heiko Feitkenhauer, et al. "On-Line Titration of Volatile Fatty Acids for the Process Control of Anaerobic Digestion of Plants." *Water Research* 36 (2002) 212-218.
M.A. Pereira, et al. "Anaerobic Biodegration of Oleic and Palmitic Acids: Evidence of Mass Transfer Limitations Caused by Long Chain Fatty Acid Accumulation onto the Anaerobic Sludge." Aug. 31, 2005, http://www.interscience.wiley.com. DOI: 10.1002/abit.20548.
Arjen Rinzema, et al. "Bacterial Effect of Long Chain Fatty Acids in Anaerobic Digestion." 913 Water Environment Research 66 (1994) Jan./Feb. No. 1, pp. 40-49.

* cited by examiner

*Primary Examiner*—Herbert J. Lilling
(74) *Attorney, Agent, or Firm*—Harness, Dickey & Pierce, P.L.C.

(57) ABSTRACT

A method of producing biogas by anaerobic digestion of organic matter includes adding cobalt, iron and hydrochloric acid to an organic matter; bringing the organic matter in contact with biogas-producing bacteria; and digesting the organic matter under anaerobic conditions in a reactor while producing biogas and a digested sludge. A device for producing biogas includes a reactor being adapted for containing the organic matter in the form of a sludge while the sludge is digested. The device includes a feeding device for adding cobalt, iron and hydrochloric acid to the organic matter, and an agitator for mixing the added cobalt, iron and hydrochloric acid with the organic matter. An additive, which is adapted for being added to a device for producing biogas by anaerobic digestion, includes cobalt, iron and hydrochloric acid in an aqueous solution.

8 Claims, 3 Drawing Sheets

METHOD, A DEVICE AND AN ADDITIVE FOR DIGESTING ORGANIC MATTER

FIELD OF THE INVENTION

The present invention relates to a method of producing biogas by anaerobic digestion of organic matter.

The present invention also relates to an additive adapted for being added to a device for producing biogas by anaerobic digestion of organic matter.

The invention further relates to a device for producing biogas by anaerobic digestion of organic matter, said device comprising a sealable, essentially gas-tight reactor having an inlet for organic matter and outlets for produced biogas and formed digested sludge, the reactor being adapted for containing the organic matter in the form of a sludge while said sludge is digested.

BACKGROUND OF THE INVENTION

Anaerobic digestion of organic matter may be used for different purposes and with many different types of organic materials. For example anaerobic digestion may be used for decreasing the volume of a waste material, such as a food production waste sludge or a domestic waste-water. Another example is the use of anaerobic digestion for to produce biogas using suitable crops. A general desire with all these processes is to obtain a high amount of biogas and a high degree of digestion, i.e. a low amount of organic material in the digested sludge.

EP 0 970 922 A2 describes a process for anaerobic digestion of organic waste, such as kitchen refuse. It is noted that sometimes the amount of trace metals available is not sufficient for the micro organisms involved in digestion and methane formation. EP 0 970 922 A2 proposes to add complexing agents and/or to add trace metals to arrive at a concentration of Co, Ni, Fe, Mn of about 1 ppm.

A problem with the process of EP 0 970 922 A2 is that it does not provide the optimum conditions for anaerobic digestion with different materials and operating conditions. Therefore the process of EP 0 970 922 A2 may sometimes provide too high consumption of trace metals still not providing for efficient digestion.

SUMMARY OF THE INVENTION

An object of the present invention is to provide a method of anaerobic digestion of organic matter by which method the production of biogas is increased without an excess trace metal consumption.

This object is achieved by a method of producing biogas by anaerobic digestion of organic matter, the method being characterised by adding cobalt, iron and hydrochloric acid to an organic matter in such a manner that the ratio between the added cobalt and iron becomes 1:80 to 1:15000 on a weight basis, and that the ratio between the added iron and hydrochloric acid becomes 1:3 to 300:1 on a weight basis, bringing the organic matter in contact with biogas-producing bacteria, and digesting the organic matter under anaerobic conditions in a reactor while producing biogas and a digested sludge.

An advantage of the present invention is that the amount of biogas produced per ton of organic matter increases surprisingly much due to the combined addition of cobalt, iron and hydrochloric acid. The digestion produces digested sludge as an end-product. The present invention has been found to decrease the amount of undigested organic matter in the end-product, thus producing an end-product which is more useful as a fertilizer.

A further object of the present invention is to provide an additive which is adapted for being added to a device for producing biogas by anaerobic digestion of organic matter and which additive is operative for making the anaerobic digestion more efficient.

This object is achieved by an additive adapted for being added to a device for producing biogas by anaerobic digestion of organic matter, the additive being characterised in that it comprises cobalt, iron and hydrochloric acid, the ratio of cobalt to iron being 1:80 to 1:15000 on a weight basis, the ratio of iron to hydrochloric acid being 1:3 to 300:1 on a weight basis.

An advantage of this additive is that it has been found to provide a simple, yet effective way of increasing the production of biogas of a device in which organic matter is digested under anaerobic conditions. The use of the additive decreases the risk that mistakes are made in the operation of the plant. Preferably said additive comprises cobalt, iron and hydrochloric acid in an aqueous solution. An advantage of the aqueous solution is that the aqueous solution is comparably easy to handle by the operators, and that it is easy to obtain accurate control of the dosing of the additive to the device for producing biogas.

Another object of the present invention is to provide a device for producing biogas, the device being more efficient in digesting organic matter than the devices of the prior art.

This object is achieved by a device for producing biogas by anaerobic digestion of organic matter, said device comprising a sealable, essentially gas-tight reactor having an inlet for organic matter and outlets for produced biogas and formed digested sludge, the reactor being adapted for containing the organic matter in the form of a sludge while said sludge is digested, the device being characterised in that it further comprises feeding means for adding cobalt, iron and hydrochloric acid to the organic matter, an agitator for mixing the added cobalt, iron and hydrochloric acid with the organic matter, a sampling means for taking out at least one sludge sample from the reactor, and an analyser which is operative for the analysis of the amount of at least one organic fatty acid, of the type having more than 10 carbon atoms, in said sludge sample, the device further comprising a control unit which is operative for controlling said feeding means to supply a suitable amount of cobalt, iron and hydrochloric acid in response to said analysis of the amount of at least one organic fatty acid, of the type having more than 10 carbon atoms, in said sludge sample.

An advantage of this device is that it is more efficient in producing biogas than the known devices. This means that device according to the invention may produce more biogas than a known device of comparable size. A further advantage is that costs for chemicals are kept low, since the chemicals support each other as regards their effect, thereby providing an advantageous economy for the operation of the device. According to a preferred embodiment the feeding means simultaneously feed the cobalt, iron and hydrochloric acid to the reactor or to a tank in which organic matter to be introduced in the reactor is stored.

Further embodiments and advantages of the invention will become-apparent from the description below and the appended claims.

BRIEF DESCRIPTION OF THE DRAWINGS

The invention will now be described in more detail with reference to the appended drawings in which.

DETAILED DESCRIPTION OF THE INVENTION

Figure 1:
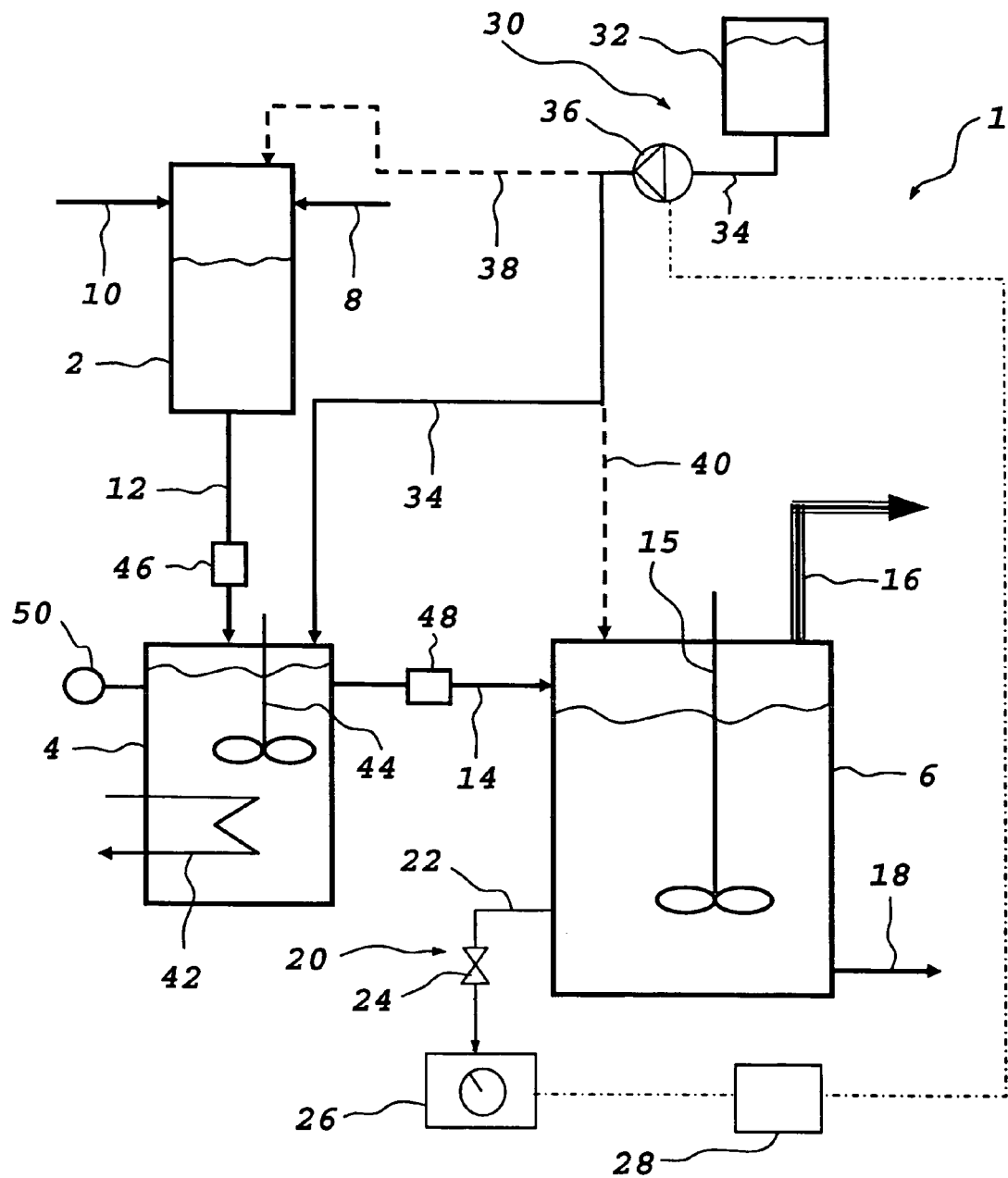
FIG. 1 is a schematic representation of a device according to one embodiment of the invention.

In the present application, the unit "% by weight TS" relates to the dry solids content (total solids) of a material. The dry solids content of a material is measured according to Swedish standard SS 02 81 13 by the material being weighed before measuring and then being heated at 105° C. for 20 h so that water evaporates. The material is then weighed once more. The dry solids content in % by weight TS is then calculated as follows $$\% \text{ by weight } TS = \frac{\text{weight after heating at } 150° \text{ C.}}{\text{weight before heating}} * 100\%$$

For instance, 90% by weight TS relates to a material where 90% of the original weight of the material remains after heating the material at 105° C. for 20 h.

In the present application, the unit "% by weight VS" relates to the content of volatile organic matter of a material, below called the volatile solids content. To determine the volatile solids content, first the dry solids content of the material is determined and then its fixed solids. The fixed solids can be determined according to Swedish Standard SS 02 81 13 by a material which has been evaporated at 105° C. for 20 h as stated above being calcined for 2 h at 550° C. The volatile solids content relates in the present application to the dry weight of the material, i.e. the weight after evaporation at 105° C. for 20 h, reduced by the fixed solids and then divided by the dry weight of the material, i.e. the weight after evaporation at 105° C. for 20 h. The volatile solids content of the material in % by weight VS is thus calculated as follows:

$$\% \text{ by weight } VS = \frac{\text{weight after } 105° \text{ C.} - \text{weight after } 550° \text{ C.}}{\text{weight after } 105°} * 100\%$$

For instance, a volatile solids content of 85% by weight VS means that 85% of the dry weight of the material, i.e. the weight of the material after heating at 105° C. for 20 h, consists of organic, volatile compounds while 15% consists of fixed solids.

The unit "g of volatile solids per day" relates, analogously with the unit % by weight VS, to an amount of volatile organic matter in grams per day as stated above. The amount of volatile organic matter supplied to the reactor, i.e. g of volatile solids, determines how much biogas can be produced since the biogas is produced from the volatile organic matter (and not from the fixed solids or the water contents).

By "degree of digestion" is meant, in the present application, the amount of material supplied to a digestion reactor that is converted into biogas in the digestion chamber. If, for instance, 10 g of volatile solids per day is supplied to a reactor in the form of digestible material and the digested sludge removed from the reactor contains correspondingly 2 g of volatile solids per day, the degree of digestion is 80%. The bacteria entrained by removed digested sludge contain some g of volatile solids, and therefore a degree of digestion of 100% according to the above definition cannot be achieved in practice.

By "substrate" is, in the present description, meant all that what is fed to a reactor for being digested under anaerobic conditions. Thus "substrate" includes organic matter, such as animal material, plant material, animal faeces, sewage sludge, industrial waste sludge etc, and any water used to dilute such components. Any additives added to improve the digestion process, without being digested, are not regarded as "substrate" in the present description.

According to the present invention organic matter is digested in a reactor. It has been found that the combination of adding cobalt, iron and hydrochloric acid to the organic matter and bringing the organic matter in contact with biogas-producing bacteria provides for an increased production of biogas from a certain amount of organic material fed to the reactor. Further the end-product, the digested sludge, is digested to a higher degree and is thus more suitable for use as a fertilizer.

While the addition of a fixed amount of cobalt is known, the combination of adding cobalt, iron and hydrochloric acid is novel and inventive and provides surprising benefits for the digestion, as will be described below.

According to one embodiment of the present invention a device for producing biogas by anaerobic digestion of organic matter comprises feeding means for adding, substantially simultaneously, cobalt, iron and hydrochloric acid to the organic matter and an agitator located inside a reactor for mixing the added cobalt, iron and hydrochloric acid with the organic matter. The feeding means and the agitator makes it possible to distribute the cobalt, iron and hydrochloric acid substantially even in the organic matter. By feeding the cobalt, iron and hydrochloric acid substantially simultaneously and mixing it with the organic matter by means of the agitator a preferable distribution of the added chemicals is enabled. This improves the digestion and decreases the risk that part of the organic matter gets "poisoned" due to overfeeding any of the added chemicals.

According to one embodiment of the present invention an additive adapted for being added to a device for producing biogas by anaerobic digestion comprises cobalt, iron and hydrochloric acid in an aqueous solution. The additive has several advantages in that it is ensured that all three components, cobalt, iron and hydrochloric acid, are added simultaneously and in the correct proportions in relation to each other. This decreases the risk that any process problems would upset the digestion process. Further the device for digestion of organic matter could be made much simpler since only one feeding means can manage to feed all three chemicals. In practical operation the type of organic matter fed to a specific digestion plant is often rather stable over time. Thus the preferred relation between the amount of cobalt, iron and hydrochloric acid is often quite stable over time. This means that the addition of the additive to the reactor may be controlled by means of one measurement only, for example iron content, based on which measured content the addition of the additive may be controlled.

According to one embodiment of the invention the addition of cobalt is based on a measurement of the concentration of an organic fatty acid having more than 10 carbon atoms. It has been found, surprisingly, that the concentration of cobalt in the sludge is often not the best measure of whether the amount of cobalt is sufficient for obtaining an efficient digestion. On the other hand it has been found that the concentration of organic fatty acids having more than 10 carbon atoms is an efficient indication on whether the amount of cobalt added should be increased or not. Organic fatty acids having more than 10 carbon atoms include, among others, palmitic acid, stearic acid, oleic acid and linoleic acid. In particular the saturated organic fatty acids, such as lauric acid, myristic acid, palmitic acid, stearic acid and arachidic acid have proven to be good indicators of whether the cobalt content is sufficient or not. In particular it has proven suitable to measure the content of palmitic acid ($C_{16}H_{32}O_2$) or stearic acid ($C_{18}H_{36}O_2$). Both these acids have proven to give a very quick response to the content of cobalt. Preferably the amount of cobalt added should be controlled to such an amount that the content of palmitic acid is less than 1500 mg/l. The content of palmitic acid has been found to be coupled to the content of stearic acid, and other saturated organic fatty acids having more than 10 carbon atoms, in such a way that a content of less than 1500 mg/l palmitic acid means that the content of stearic acid is also less than 1500 mg/l. Thus it is not necessary to measure the content of exactly palmitic acid, the content of another organic fatty acid could be measured instead and could be controlled in such manner that the content of palmitic acid will also arrive below the desired amount. Still more preferably the addition of cobalt is controlled to provide a content of palmitic acid of less than 1000 mg/l. Most preferably the content of each individual saturated organic fatty acid having more than 10 carbon atoms is less than 1500 mg/l, more preferably less than 1000 mg/l. Normally a cobalt addition sufficient to manage these limits corresponds to 0.1 to 0.6 g of Co added per $m^3$ of substrate fed to the reactor.

It should be emphasized that an addition of cobalt in itself is not sufficient for obtaining the improvements in the amount of biogas produced according to the present invention. Thus the values described above for content of palmitic acid and stearic acid requires that iron and hydrochloric acid are added as well as cobalt.

Preferably the content of iron added to the reactor is controlled to correspond to at least 500 g of Fe added per $m^3$ of substrate fed to the reactor. The substrate fed to the reactor comprises mostly organic matter and water and generally has an overall dry solids content in the range of 3-30% by weight TS, often 8-15% by weight TS. The above indicated addition of Fe has proven to be suitable for this range of dry solids content. At lower contents of iron there is a certain risk that hydrogen sulphide, $H_2S$, will form in the reactor. Such a formation will deteriorate the quality of the biogas and also decreases the efficiency of the digestion, an efficiency which cannot be restored by simply increasing the addition of cobalt. Preferably the amount of iron added corresponds to less than 4000 g of Fe added per $m^3$ of substrate fed to the reactor. An amount of iron that is higher than this amount has been found to increase the operating costs without further improving the efficiency of the biogas-producing bacteria. Preferably the amount of iron added to the reactor is controlled so as to obtain a content of $H_2S$ in the produced biogas of 50-100 ppm. In addition to decreasing the formation of $H_2S$ the iron also works as a nutrient to the biogas-producing bacteria.

Hydrochloric acid is preferably added to such an amount that it corresponds to an addition of at least 10 g HCl (as free acid) added per $m^3$ of substrate fed to the reactor. The addition of HCl has been found to improve the digestion since it neutralises any ammonia formed during decomposition of proteins. The ammonia formed has been found to have a tendency to poison the biogas-producing bacteria. By adding the hydrochloric acid the ammonia is neutralized and converted to ammonium ions, $NH_4^+$, and the pH is somewhat decreased in the sludge, thereby preventing any poisoning of the biogas-producing bacteria. Consequently the addition of hydrochloric acid avoids, by decreasing the pH slightly, that the sludge is acidified. The amount of hydrochloric acid added is preferably set to such an amount that the pH in the sludge in the reactor is about 0.01-1.5 pH units lower than the pH would have been without the addition of hydrochloric acid. Preferably the added amount of hydrochloric acid corresponds to less than 1500 g HCl (as free acid) added per $m^3$ of substrate fed to the reactor. Preferably the pH in the reactor is controlled to be below pH 8.0 but above pH 6.5 in order to obtain good conditions for the biogas-producing bacteria.

The addition of cobalt, iron and hydrochloric acid according to one embodiment of the present invention provides advantageous effects which go beyond what would be expected based on just adding the effects of each component when used individually.

The sampling of the sludge from the reactor could be made fully automatically or more or less manually. Due to the long residence times in the reactor, often about 10-60 days, the conditions usually do not change very rapidly. Thus a sample may be taken at a frequency of twice per day to once per week. If the substrate fed to the reactor is known to vary much in its properties samples should be taken more often. Each sample should be analysed for the content of an organic fatty acid having more than 10 carbon atoms, such as palmitic acid or stearic acid, and preferably, but not necessarily, also for iron content and pH value. Based on the analysis performed the addition of cobalt, iron and hydrochloric acid is adjusted. The adjustment could be made by means of an automatic controller or manually. If the additive comprising cobalt, iron and hydrochloric acid in an aqueous solution is used the amount of this additive to be added is set in relation to which of the three components cobalt, iron and hydrochloric acid, which is most scarce in the sludge, based on the analysis. As noted above, however, if the additive has such a composition that it is well suited for the organic matter in question it is usually not necessary to measure more than one parameter, such as palmitic acid indicating the need for cobalt, and control the addition of the additive based on that one parameter.

The additive is preferably formed by mixing cobalt, iron, hydrochloric acid and water in such amounts that a suitable content of cobalt, iron and hydrochloric acid is obtained in the additive. The cobalt is preferably present in the form of $Co^{2+}$ ions. The iron is preferably present in the form of $Fe^{3+}$ or $Fe^{2+}$ ions, or as a mixture of both ions. Most preferably at least 75% of the iron is present as $Fe^{2+}$.

When forming the additive the cobalt, preferably in the form of $CoCl_2 \times 6H_2O$ or $CoCl_2$, is added to water. Other cobalt salts may be used as well. The iron is preferably added as $FeCl_3 \times 6H_2O$ or $FeCl_2 \times 4H_2O$ in solid form or as an aqueous solution of $FeCl_3$ or $FeCl_2$ in water, still more preferably in combination with an inorganic acid. This inorganic acid is preferably hydrochloric acid, HCl, such that at least a portion of the hydrochloric acid that is to be added to the additive is added as hydrochloric acid together with the iron. The hydrochloric acid is preferably added to the solution as a hydrochloric acid of technical grade. It will be appreciated that the cobalt, iron, hydrochloric acid and water in the additive is added in amounts to provide the desired concentration in the final additive. Other solvents than water, such as alcohols, may also be utilized in the preparation of the additive, but water is often the preferred solvent for the additive.

A preferable additive comprises cobalt, Co, and iron, Fe, in a ratio of 1:80 to 1:15000 on a weight basis. The low amount of cobalt in relation to the iron has the advantage of reducing the risk of poisoning by cobalt, since the cobalt will always be present in a very low concentration.

Furthermore, the additive preferably comprises iron, Fe, and hydrochloric acid, HCl, in a ratio of 1:3 to 300:1 on a weight basis. This ratio has proven to give a suitable relation between iron and hydrochloric acid for the organic matter in most cases and also provides for keeping all components of the additive dissolved in the additive without problems of precipitation. The ratio between cobalt, Co, and hydrochloric acid, HCl, i.e., Co:HCl, in the additive is preferably 1:1 to 1:15000 on a weight basis.

Cobalt, iron and hydrochloric acid may also be added separately to the organic matter, i.e., not in the form of an additive comprising all three substances, but as three separate components. Cobalt, iron and hydrochloric acid may also be added to the organic matter in the form of one mixture containing two of those three substances, and one component containing the last one of those three substances. In such cases of not using an additive it is preferable that the ratio between the added cobalt and iron, i.e., Co:Fe, is 1:80 to 1:15000 on a weight basis, that the ratio between the added iron and hydrochloric acid, i.e., Fe:HCl, is 1:3 to 300:1 on a weight basis, and that the ratio between the added cobalt and hydrochloric acid, i.e., Co:HCl, is 1:1 to 1:15000 on a weight basis.

According to a preferred embodiment the additive comprises iron, calculated as Fe ions (i.e. $Fe^{2+}$ or $Fe^{3+}$ ions), in an amount of 5 to 15% by weight, cobalt, calculated as $Co^{2+}$ ions, in an amount of 0.001 to 0.050% by weight, and hydrochloric acid, calculated as HCl, in an amount of 0.05 to 15% by weight. This composition provides for small risk of poisoning the biogas producing bacteria, low health hazards to operators and a rather low amount of the additive that needs to be added per hour.

For a plant digesting a substrate that is mainly based on green matter a certain composition of the additive is particularly suitable. By "green matter" is meant plants and parts of plants of the type using photosynthesis for producing the plant matter. The green matter can advantageously consist of various agricultural products, such as ensilage, straw, grain, grain offal, rape, sunflowers, maize, sugar-beets, turnips, cabbage, potatoes, molasses, peas, beans, lentils, flax, lupins and pasture plants, such as lucerne, grass and clover. For a plant digesting green matter the requirement for iron and hydrochloric acid has been found to be quite low, while the requirement for cobalt is higher, relatively speaking. When operating a biogas plant in which at least 60% of the volatile solids, more preferably at least 90% of the volatile solids, i.e. at least 60%, and more preferably at least 90%, of the supplied g of volatile solids per day, fed to the reactor is green matter, as defined above, it is preferable to add cobalt, iron and hydrochloric acid in such amounts that the ratios, on a weight basis, of the added substances become: Co:Fe=1:500 to 1:6000, Fe:HCl=5:8 to 240:1, more preferably Fe:HCl=5:1 to 240:1, and Co:HCl=1:5 to 1:4000, more preferably Co:HCl=1:5 to 1:500. Preferably cobalt, iron and hydrochloric acid are mixed with a solvent, preferably water, to form an additive, which is suitable for being added to such a biogas plant in which at least 60%, and more preferably at least 90%, of the supplied g of volatile solids per day fed to the reactor is green matter. Such an additive would preferably comprise iron, cobalt and hydrochloric acid in such amounts that the ratios, on a weight basis, of the substances of the additive become: Co:Fe=1:500 to 1:6000, Fe:HCl=5:8 to 240:1, more preferably Fe:HCl=5:1 to 240:1, and Co:HCl=1:5 to 1:4000, more preferably Co:HCl=1:5 to 1:500. The additive adapted for a biogas plant in which at least 60%, more preferably at least 90%, of the volatile solids, i.e. at least 60%, more preferably at least 90%, of the supplied g of volatile solids per day, fed to the reactor is green matter, as defined above, would advantageously comprise iron, calculated as Fe ions, in an amount of 5 to 12% by weight, cobalt, calculated as $Co^{2+}$ ions, in an amount of 0.002 to 0.010% by weight, and hydrochloric acid, calculated as HCl, in an amount of 0.05 to 8% by weight, more preferably in an amount of 0.05 to 1% by weight. Such a biogas plant, in which at least 60%, and more preferably at least 90%, of the supplied g of volatile solids per day fed to the reactor is green matter, could additionally digest up to 40% of cow dung, sewage sludge, and/or dairy waste. By "dairy waste" is meant milk, cream, whey, and processed milk products. Furthermore, it would also be possible to digest up to 10% of organic material of "animal origin", as defined hereinafter, together with the green matter, and, optionally, together with the dairy waste, cow dung and/or sewage sludge.

A special type of green matter is the so called distillers waste. Distillers waste is green matter, e.g. grain, sugar-beets, or potatoes, that has been subjected to a fermentation process for the purpose of producing ethanol. The fermentation process only partly transforms the green matter into ethanol, and, thus, much of the digestible organic matter present in the original green matter is still available in the distillers waste. Consequently, it is attractive to subject distillers waste to an anaerobic digestion for the purpose of producing biogas. Since distillers waste is basically grain, potatoes, etc., as the case may be, that has been fermented, the requirement for cobalt, iron and hydrochloric acid in the digestion of distillers waste is substantially the same as in the digestion of the corresponding original type of green matter. Thus, the additive composition which is described above and which is suitable for the digestion of green matter can be utilized also when digesting distillers waste, which is a special type of green matter that is similar to the original green matter when it comes to the need for cobalt, iron, and hydrochloric acid. The distillers waste could be digested together with other types of green matter, e.g., together with grain or grain offal, wherein the amount of distillers waste could be anything from 0 to 100%. The distillers waste could also be digested together with suitable amounts of other types of organic matter such as cow dung and dairy waste. It is also possible to digest solely distillers waste in a digestion plant.

For a plant digesting a substrate which contains material of animal origin to an extent which is not negligible another composition of the additive is suitable. By "animal origin" is meant, in the present description, slaughterhouse waste, including blood, bowels, skin, fat, muscular tissue etc; complete animal bodies; and parts of animal bodies that have been processed, for instance to form different food products. Animal faeces, such as cow dung, is not regarded as "animal origin" in the present description. For a plant digesting some material of animal origin the requirement for iron, hydrochloric acid and cobalt has been found to be quite high. When operating a biogas plant in which at least 20% of the volatile solids, i.e. at least 20% of the supplied g of volatile solids per day, fed to the reactor is of animal origin, as defined above, it is preferable to add cobalt, iron and hydrochloric acid in such amounts that the ratios, on a weight basis, of the added substances become: Co:Fe=1:160 to 1:7500, Fe:HCl=8:15 to 15:1, and Co:HCl=1:20 to 1:7500. Preferably cobalt, iron and hydrochloric acid are mixed with a solvent, preferably water, to form an additive, which is suitable for being added to such a biogas plant in which at least 20% of the supplied g of volatile solids per day fed to the reactor is of animal origin. Such an additive would preferably comprise iron, cobalt and hydrochloric acid in such amounts that the ratios, on a weight basis, of the substances of the additive become: Co:Fe=1:160 to 1:7500, Fe:HCl=8:15 to 15:1, and Co:HCl=1:20 to 1:7500. The additive adapted for a biogas plant in which at least 20% of the volatile solids, i.e. at least 20% of the supplied g of volatile solids per day, fed to the reactor is of animal origin, as defined above, would advantageously comprise iron, calculated as Fe ions, in an amount of 8 to 15% by weight, cobalt, calculated as $Co^{2+}$ ions, in an amount of 0.002 to 0.050% by weight, and hydrochloric acid, calculated as HCl, in an amount of 1 to 15% by weight. In addition to the organic matter of animal origin, which constitutes at least 20% of the volatile solids, i.e. at least 20% of the supplied g of volatile solids per day, fed to the reactor, the biogas plant could digest cow dung, green matter, as defined hereinbefore, dairy waste, sewage sludge, etc.

It will be appreciated that it would be possible to design a suitable composition for the additive for each type and composition of material to be digested. On the other hand it has been found that one additive suited for digestion of mainly green matter, as described above, and one additive suited for digestion of a considerable amount of material of animal origin, as described above, is enough to cover most different combinations of organic matter to be digested. For example, in a biogas plant in which at least 90% of the volatile solids, i.e. at least 90% of the supplied g of volatile solids per day, fed to the reactor is dairy waste, as defined above, it is preferable to add cobalt, iron and hydrochloric acid in such amounts that the respective ratios of cobalt, iron and hydrochloric acid are similar to those ratios described hereinbefore for a biogas plant in which at least 60% of the volatile solids, more preferably at least 90% of the volatile solids, i.e. at least 60%, and more preferably at least 90%, of the supplied g of volatile solids per day, fed to the reactor is green matter. Consequently, an additive comprising cobalt, iron and hydrochloric acid in such ratios that are suitable for the digestion of green matter could also be utilized when digesting dairy waste.

In digestion in a tank reactor, the dry solids content of the digested sludge in the reactor is suitably about 4-30% by weight TS, preferably about 5-10% by weight TS. In an agitated and continuously operating tank reactor, the digested sludge removed from the reactor will have essentially the same dry solids content as the digested sludge in the reactor. Supply of new substrate to the tank reactor is thus made continuously, i.e. as an even inflow, or semi-continuously, i.e. in small portions, preferably from a premixing tank. Removal of sludge from the tank reactor can be effected continuously, i.e. as an even outflow, or semi-continuously, i.e. in small portions.

When starting the process, an active culture of bacteria is usually introduced into the reactor. This culture of bacteria may consist of, for instance, digested sludge from a parallel digestion plant, digested sludge from a municipal wastewater treatment plant or cow-dung. As the culture of bacteria grows, an increasingly greater amount of the organic matter to be digested can be supplied to the reactor.

The method according to the invention can be carried out in a plurality of reactors connected in series. In such a case the additive is preferably added to the first reactor in the series. However, it is often advantageous to carry out the anaerobic digestion in a single step since this saves equipment and maintenance costs.

DESCRIPTION OF PREFERRED EMBODIMENTS

FIG. 1 shows a device 1 according the present invention. The device 1 comprises a mixing tank 2, a heated sanitation tank 4 and a reactor 6. Organic matter is fed to the mixing tank 2 via a pipe 8. For instance the organic matter could be slaughter-house waste, crops, cereals, manure, sewage sludge, food industry waste etc. Water is added, if necessary, via a pipe 10 to the mixing tank 2 to obtain a substrate having the desired dry solids content, typically 3-30% by weight TS, more often about 8-15% by weight TS. The substrate forms a slurry in the mixing tank 2 which is then fed, intermittently, to the sanitation tank 4 via a pipe 12. In the sanitation tank 4 the slurry is heated to a temperature of more than 70° C., usually about 72° C., and is kept at that temperature for at least one hour in order to kill any harmful micro-organisms, such as bacteria and viruses. Thus the sanitation tank 4 operates in a batch mode. When the slurry containing the organic matter has been properly sanitized it is pumped via a pipe 14 to the reactor 6. Thus the pipe 14 forms an inlet for organic matter to the reactor 6, which is a sealable, essentially gas-tight reactor that is provided with an agitator 15 making the reactor 6 function as a tank reactor. The reactor 6 is provided with an outlet pipe 16 for the produced biogas containing mainly methane, $CH_4$, hydrogen, $H_2$, and carbon dioxide, $CO_2$. The reactor 6 also has an outlet pipe 18 for digested sludge. Although the sanitation tank 4 works in a batch mode, with a residency time of a little more than 1 hour, the reactor 6 can be considered to be a continuously working reactor since the average residence time in the reactor 6 is 5-100 days, preferably about 10-60 days, which is much more than the residence time in the sanitation tank 4. The reactor 6 operates at a temperature of about 30-400° C., preferably about 37° C.

The device 1 further comprises a sampling means 20 for taking samples of the sludge in the reactor 6. The sampling means 20 comprises a pipe 22 and a valve 24, which may be a manual valve or an automatic valve. With the help of the sampling means 20 samples of the sludge may be taken out from the reactor 6 on a regular basis. The samples are analysed by means of an analyser 26, such as a gas chromatograph, in order to measure the concentration of at least one organic fatty acid with more than 10 carbon atoms. The result of the analysis is fed to a control unit 28. Based on the content of the at least one fatty acid the control unit 28 sends a control signal to a feeding device 30. The feeding device 30 comprises a storage tank 32 for storing an additive, a pipe 34 connected to the storage tank 32 and a pump 36 for pumping the additive from the storage tank 32 to the sanitation tank 4 via the pipe 34 in response to the control signal from the control unit 28. The additive, which is described in detail above, comprises iron, cobalt and hydrochloric acid in an aqueous solution.

As illustrated in FIG. 1 the sludge sample may be automatically fed, by means of the sampling means 20, to the analyser 26. It is, however, also possible to take out a sample manually from the sampling device 20 and to bring this to an analyser located in a lab. The measured content of the organic fatty acid is then manually entered into the control unit 28. As a further alternative an operator, having analysed the sample, may manually control the feeding device 30 to a suitable feeding rate.

As described above the additive may be fed via the pipe 34 to the sanitation tank 4. According to alternative embodiments the additive could be fed via the pipe 38 to the mixing tank 2 or via the pipe 40 to the reactor 6. It is often preferred to feed the additive to the sanitation tank 4, as will be described below.

The sanitation tank 4 is provided with a heater 42 for heating the substrate in the sanitation tank 4 to the desired temperature for sanitation, and an agitator 44 for avoiding that any portions of the organic matter sedimentates in the tank 4. Thanks to the agitator 44 the additive, fed via the pipe 34, gets well mixed with the organic matter before the organic matter enters the reactor 6. This avoids a locally too high concentration of the additive, and a resulting negative effect on the biogas-producing bacteria, in the reactor 6.

In an alternative embodiment the amount of the additive supplied via the pipe 34, or any one of the pipes 38 and 40, may be controlled based on the volume of substrate fed to the reactor 6 rather than being based on the measured content of organic fatty acids in the sludge. If the substrate fed has stable properties the amount of the additive to be added is to a high degree proportional to the volume of substrate fed to the reactor 6. The pipe 12 is provided with a flow meter 46 and the pipe 14 is provided with a flow meter 48. Further the sanitation tank 4 is provided with a level meter 50. Thus it is possible to determine the volume of substrate fed to the sanitation tank 4, via the pipe 12, the volume of substrate fed from the sanitation tank 4 to the reactor 6, via the pipe 14, and the volume of substrate in the sanitation tank 4 at any given moment. By means of the meters 46, 48, 50 it is possible to calculate how large volume, in $m^3$ or a similar unit, of substrate that has been fed to the sanitation tank 4. By setting the amount of the additive to be added per $m^3$ of substrate fed to the sanitation tank 4, which is essentially the same as the volume fed to the reactor 6, it is possible to obtain a simple control of the additive to be added. The pump 36 would thus be controlled by a signal, e.g. from the flow meter 46, indicating the volume of substrate added to the sanitation tank 4. Analysis of the organic fatty acids in the sludge could then be made quite seldom just to ensure that conditions remain stable and that the content of the fatty acids remains below the desired limits.

Figure 2:
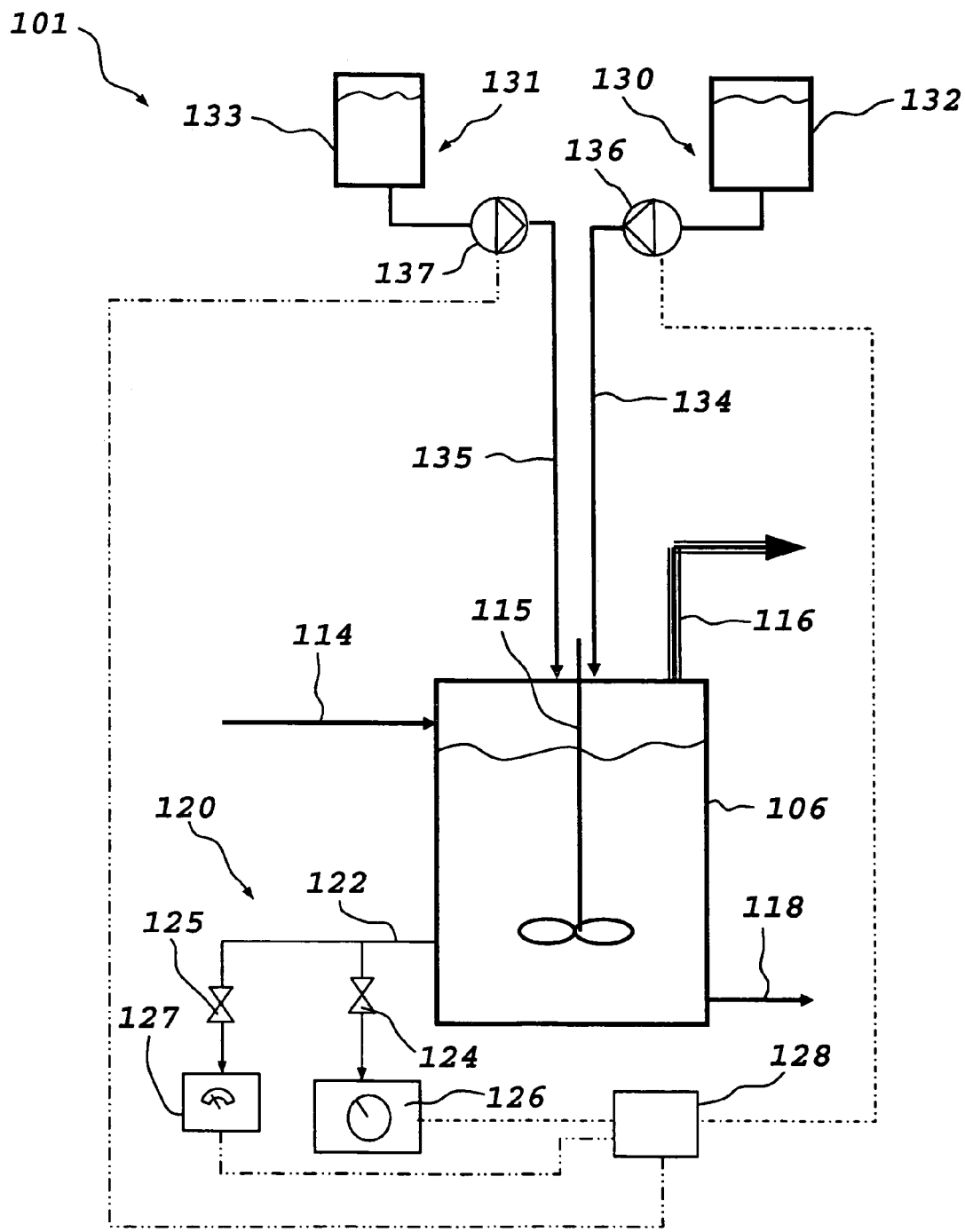
FIG. 2 is a schematic representation of a device according to an alternative embodiment of the invention.

FIG. 2 illustrates an alternative embodiment of the invention in the form of a device 101. The device 101 has a mixing tank and a sanitation tank that are of the same design as that of the device 1 and that are not shown in FIG. 2. The device 101 further comprises a reactor 106 having an inlet 114 for organic matter, an outlet 116 for biogas, and an outlet 118 for digested sludge. Samples of the sludge in the reactor 106 are taken on a regular basis by means of a sampling means 120. The sampling means 120 comprises a pipe 122 and a first valve 124 and supplies samples to a first analyser 126, which, in a similar manner as the analyser 26, analyses the amount of at least one fatty acid with more than 10 carbon atoms. The sampling means 120 further comprises a second valve 125 by which samples of the sludge may be supplied to a second analyser 127. The second analyser 127 is adapted for analysing the content of iron and/or the pH-value of the sludge. Based on the amount measured by the analyser 126 a control unit 128 sends a first control signal to a first feeding device 130. The first feeding device 130 comprises a storage tank 132 for storing cobalt in an aqueous solution. In response to the control signal from the control unit 128 a pump 136 supplies a suitable amount of the cobalt solution to the reactor 106 via a pipe 134. The control unit 128 also sends a second control signal to a second feeding device 131. The second feeding device 131 comprises a storage tank 133 for storing hydrochloric acid and iron in an aqueous solution. In response to the control signal from the control unit 128 a pump 137 supplies a suitable amount of the hydrochloric acid and iron solution to the reactor 106 via a pipe 135. It will be appreciated that the pipes 134, 135 could also, according an often preferred alternative, be connected to the, not shown, sanitation tank, in accordance with principles similar to those described with reference to FIG. 1. The amount of the hydrochloric acid and iron solution to be supplied could be set based on the pH of the sludge, based on the iron content in the sludge, or based on a combination on these two values. It will be appreciated that it is also possible, as with the embodiment of FIG. 1, to make manual sampling of the sludge and bring these samples to a lab. Further it is also possible to control the feeding devices 130, 131 manually. Still further the feeding devices 130, 131 could be adapted for feeding their respective solutions to the mixing tank or the sanitation tank instead, as mentioned above. Compared with the embodiment of FIG. 1 the device 101 is more complicated and also requires two different solutions. The device 1 of FIG. 1, using only one additive, is thus in many cases the preferred embodiment.

According to a still further alternative embodiment the second feeding device 131 could be adapted for feeding an additive containing hydrochloric acid and iron and, additionally, an amount of cobalt which is lower than the amount of cobalt which is normally needed. In this alternative embodiment the first feeding device 130 would operate to "top-up" with the extra cobalt needed, upon indication that the content of organic fatty acids is about to increase above the desired limits. In a still further alternative embodiment the "top-up" could be made manually by adding cobalt in an aqueous solution from a beaker or as a powder.

An additive according to the invention could be made by pouring water into a tank and then add the different components, cobalt, iron and hydrochloric acid, in the suitable amounts. Cobalt and iron could be added either as dry salts, or as concentrated solutions. For use in a biogas plant in which 100% of the volatile solids, i.e. 100% of the supplied g of volatile solids per day, fed to the reactor is green matter a suitable additive could contain the following components:

| | |
|---|---|
| Cobalt (Co): | 0.006% by weight |
| Iron (Fe): | 10% by weight |
| Hydrochl. acid (HCl) | 0.1% by weight |
| Water | |

The above mentioned additive, adapted for digestion of green matter, is suitably added in an amount of about 5 kg additive per $m^3$ of substrate added to the reactor. The substrate fed to the reactor could, with this amount of additive added, correspond to about 6000 g of volatile solids per day per $m^3$ of reactor volume. It has proven suitable, in some cases, to utilize an additive containing a somewhat higher concentration of hydrochloric acid, such as about 1% by weight of HCl, or even up to 8% by weight of HCl, when digesting green matter.

For use in a biogas plant in which 50% of the volatile solids, i.e. 50% of the supplied g of volatile solids per day, fed to the reactor is slaughterhouse waste and 50% of the volatile solids, i.e. 50% of the supplied g of volatile solids per day, fed to the reactor is cow dung a suitable additive could contain the following components:

| | |
|---|---|
| Cobalt (Co): | 0.005% by weigth |
| Iron (Fe): | 10% by weight |
| Hydrochl. acid (HCl) | 6% by weight |
| Water | |

The above mentioned additive, adapted for digestion of waste at least part of which is of animal origin, is suitably added in an amount of about 10 kg additive per m³ of substrate added to the reactor. The substrate fed to the reactor could, with this amount of additive added, correspond to about 3000 g of volatile solids per day per m³ of reactor volume.

It will be appreciated that numerous variants of the above-described embodiments are possible within the scope of the appended patent claims.

EXAMPLE 1

Figure 3:
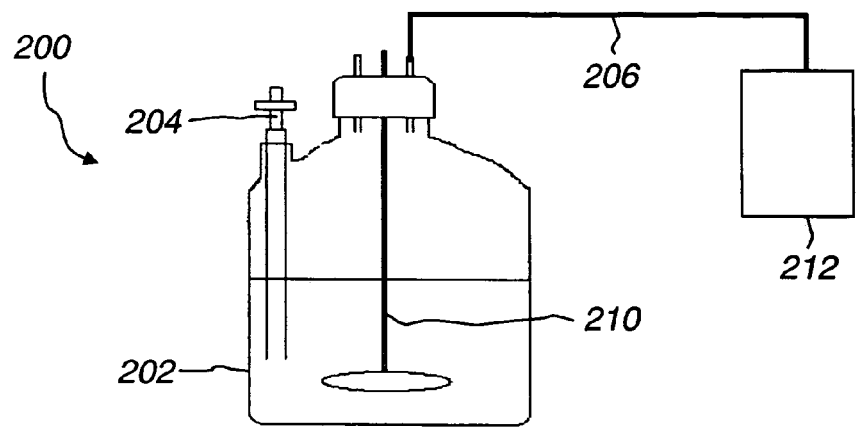
FIG. 3 is a schematic side view and illustrates an experimental device.

In a digestion experiment involving organic matter of animal origin an experimental device 200, which is shown in FIG. 3, was used. The device 200 has a gas-tight glass reactor 202 with a volume of 5 l. The liquid volume in the reactor 202 was kept constant at 3 l, thus the effective reactor volume was 3 l. A propeller agitator 210 (with a speed of 300 rpm) was used to achieve complete agitation in the reactor 202. A pipe 206 passed generated gas from the reactor 202 to a gas meter 212 measuring the volume of generated gas. A tight glass feed-through 204 was used for batch supply of sanitised ground organic matter and intermittent removal of formed digested sludge. A tempered space (not shown) was used to keep the temperature in the glass reactor 202 at 37° C.

The organic matter contained about 60% by volume of slaughterhouse waste (mainly blood, muscles, bowels and fat), cow dung (about 5% by volume) and waste from food processing industry (totally about 35% by volume). The total protein content in the substrate fed to the reactor was estimated to be about 5% by weight.

The slaughterhouse waste, the cow dung and the waste from food industry was mixed with water to obtain a substrate in the form of a slurry with a dry solids content of 13% by weight TS. About 85-90% of the dry solids content was volatile solids, i.e. the slurry had a volatile solids content of about 11% by weight VS. Consequently almost 50% of the volatile solids were proteins. About 80% of the volatile solids content, i.e. 80% of the supplied g of volatile solids per day, fed to the reactor 202 had animal origin.

60 ml of this slurry was added to the reactor 202 each day, thus corresponding to a feed of 6.6 g of volatile solids (VS) per day, which corresponded to 2200 g of VS per day and m³ of reactor volume (the effective reactor volume was 3 l as indicated above). A similar amount of digested sludge was removed each day to keep the sludge level constant in the reactor. The residence time in the reactor 202, which could be considered to be operating as a continuously working tank reactor, was about 50 days. The dry solids content of the sludge in the reactor 202 was 5% by weight TS.

Iron was added to the reactor in an amount of 54 mg per day, corresponding to 900 g of Fe added per m³ of substrate fed to the reactor 202. The content of iron, as Fe, was about 900 mg/l in the sludge in the reactor 202. Hydrochloric acid was added to the reactor 202 in an amount of 36 mg HCl per day, corresponding to 600 g of HCl added per m³ of substrate fed to the reactor. The pH of the sludge in the reactor 202 was decreased by about 0.1 pH units compared with no addition of hydrochloric acid.

Figure 4:
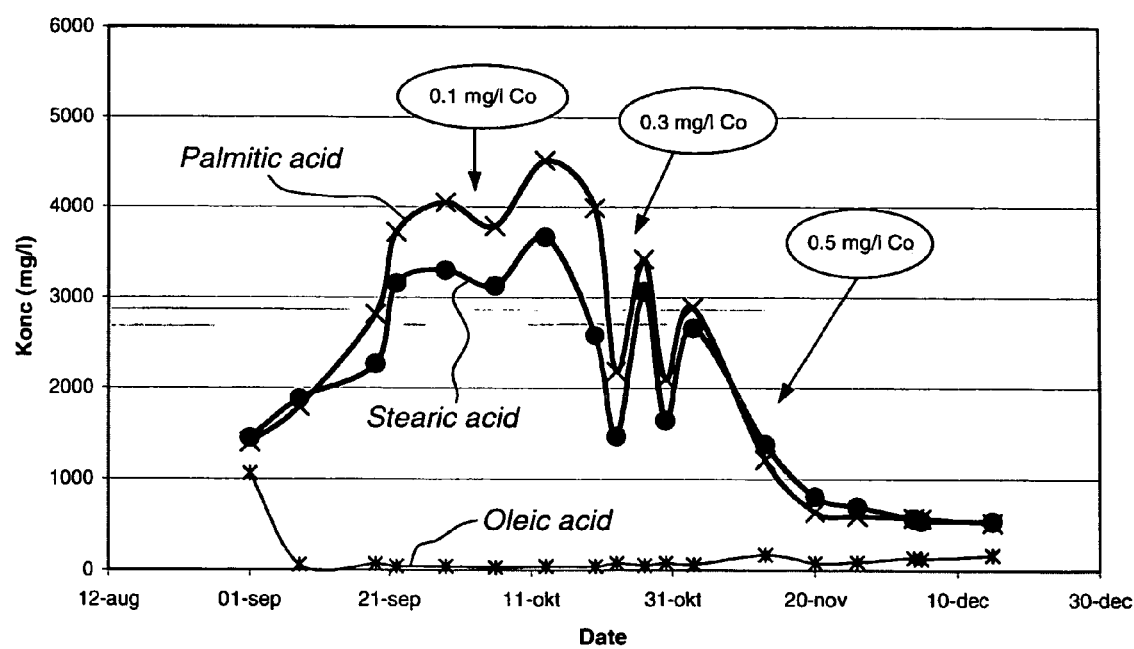
FIG. 4 is a diagram and illustrates results of tests in the experimental device.

At the start of the operation no cobalt was added at all. During this time severe problems of foaming occurred. Analysis of the sludge taken out of the reactor 202 showed that the concentration of palmitic acid and stearic acid increased steadily. FIG. 4 illustrates how the concentrations of palmitic acid and stearic acid increases steadily from the start on September 1st until September 28th. The biogas production during this period corresponded to about 500 Nm³ of biogas per ton of VS. The severe problems with foaming disturbed the gas measurement and the feeding of substrate to the reactor 202. After September 28th cobalt was added to such an amount that the concentration in the sludge in the reactor became 0.1 mg/l Co. This corresponded to about 0.1 g of Co added per m³ of substrate fed to the reactor 202. The cobalt was added as a separate aqueous solution with a concentration of about 0.05% by weight Co. The iron was added together with the hydrochloric acid from a tank separate from that of the cobalt solution in order to study the effect of the cobalt. The problems with the foaming decreased substantially. As shown in FIG. 4 the addition of cobalt stopped the increase in content of palmitic acid and stearic acid. The biogas production on October 11th was about 560 Nm³ of biogas per ton of VS. Since the concentration of palmitic acid and stearic acid was still quite high the addition of cobalt to the reactor 202 was increased to correspond to 0.3 mg/l Co in the sludge on October 28th and was then further increased to 0.5 mg/l Co in the sludge, corresponding to about 0.5 g of Co added per m³ of substrate fed to the reactor, on November 8:th. As can be seen the concentration of palmitic acid and stearic acid decreased below 1000 mg/l. At the same time the foaming in the reactor ceased completely. The biogas production on December 10th was about 1000 Nm³ of biogas per ton of VS.

From FIG. 4 it is clearly shown that the concentration of stearic acid and palmitic acid works as an indicator for what concentration of cobalt is required at the prevailing operating conditions. FIG. 4 illustrates also the concentration of oleinic acid, an unsaturated organic fatty acid, which does not provide any indication as regards the need for increased cobalt. The test results further showed that a decreased stearic acid and palmitic acid concentration was related to increased biogas production and decreased foaming. Since stearic acid and palmitic acid shows a similar response to the cobalt concentration it does not matter which one of them is measured. Correspondingly any other organic fatty acid, preferably a saturated organic fatty acid, with more than 10 carbon atoms could also be measured for the purpose of obtaining information based on which the cobalt addition could be controlled.

EXAMPLE 2

In a full-scale plant tests were conducted to evaluate the efficiency of the additive according to the invention. The full scale plant had two reactors with volume of about 3600 m³ each. The residence time was about 45 days. The general-set-up of the plant was similar to that described with reference to FIG. 1, with the exception that the sampling and analysis of the sludge was made manually and that the feeding system for feeding the additive was controlled manually based on analysis results.

Three different solutions were used during the tests: Solution A was a commercially available iron chloride solution containing $FeCl_2$ in water. The content of iron, Fe, was about 14% by weight. Solution B was a mixture of $FeCl_2$, hydrochloric acid (HCl) and water. The content of iron, Fe, corresponded to about 9% by weight and the content of hydrochloric acid, HCl, corresponded to about 6% by weight. Solution C was formed as an additive according to the invention and contained: cobalt, Co, 0.004% by weight, iron, Fe, 9% by weight, hydrochloric acid, HCl, 6% by weight, and water. Three tests were performed: Test 3 was made by adding the Solution C according to the invention. The content of palmitic acid and stearic acid in the sludge in the reactors was measured on a daily basis and the feeding of the Solution C, i.e. the additive according to the invention, was adjusted accordingly. Comparative tests 1 and 2 were performed in order to illustrate the effectiveness of the invention.

In Comparative test 2 and in Test 3 the composition of the substrate digested was the same as in Example 1, i.e. the volatile solids content was about 11% by weight VS and about 80% of the volatile solids content, i.e. 80% of the supplied g of volatile solids per day, fed to the reactor had animal origin.

In Comparative test 1 it was necessary, to avoid severe foaming problems, to have a lower amount of slaughterhouse waste and a larger amount of cow dung. Thus, in Comparative test 1 the organic matter contained about 50% by volume of slaughterhouse waste, about 25% by volume of cow dung, and about 25% by volume of waste from food processing industry. The slaughterhouse waste, the cow dung and the waste from food industry was mixed with water to obtain a substrate in the form of a slurry with a dry solids content of 12% by weight TS. About 80% of the dry solids content was volatile solids, i.e. the slurry had a volatile solids content of about 10% by weight VS. About 60% of the volatile solids content, i.e. 60% of the supplied g of volatile solids per day, fed to the reactor had animal origin in the Comparative test 1.

In Comparative test 1 the amount of solution A added to the reactor corresponded to 3 kg of solution A added per $m^3$ of substrate fed to the reactor. In Comparative test 2 the solution B was added to the reactor in an amount of 4.5 kg of solution B per $m^3$ of substrate fed to the reactor. In Test 3 the solution C was added to the reactor in an amount of 7.0 kg of solution C per $m^3$ of substrate fed to the reactor.

Table 1 below illustrates the biogas production at the three tests:

TABLE 1

| Biogas production at Tests 1-3. | | | | |
|---|---|---|---|---|
| Test No | Solution | Iron | HCl | Cobalt | Biogas prod* |
| Comp. 1 | A | Yes | No | No | 63 |
| Comp. 2 | B | Yes | Yes | No | 99 |
| 3 | C | Yes | Yes | Yes | 134 |

*Biogas production in $m^3$ biogas per ton of substrate fed to the reactors (wet basis)

As is clearly illustrated by Table 1 the simultaneous addition of iron, hydrochloric acid and cobalt according to the invention, i.e. Test 3, results in a substantial increase in the biogas production. The increase in biogas-production has two main reasons: Firstly the volatile solids content of the substrate fed to the reactor is more completely converted to biogas in Test 3, probably thanks to the components of solution C providing better conditions for the biogas-producing bacteria. Secondly solution C, used in Test 3, makes it possible to feed a substrate to the reactor in which substrate the content of easily digested volatile solids, i.e. volatile solids of animal origin, is higher compared to, in particular, Comparative test 1, in which a higher amount of the volatile solids necessarily needs to originate from cow dung, which is less easy to digest, to avoid foaming problems.

The invention claimed is:

1. A method of producing biogas by anaerobic digestion of organic matter, comprising:
   adding cobalt, iron and hydrochloric acid to an organic matter in such a manner that a ratio between the added cobalt and iron becomes 1:80 to 1:15000 on a weight basis, and that the ratio between the added iron and hydrochloric acid becomes 1:3 to 300:1 on a weight basis;
   bringing the organic matter in contact with biogas-producing bacteria; and
   digesting the organic matter under anaerobic conditions in a reactor while producing biogas and a digested sludge.

2. The method according to claim 1, wherein iron, cobalt and hydrochloric acid are added in the form of an additive containing iron, cobalt and hydrochloric acid in an aqueous solution.

3. The method according to claim 1, wherein, on a regular basis, a sample of the digested sludge is taken out of the reactor and is analysed for the content of at least one organic fatty acid having more than 10 carbon atoms, the amount of cobalt added to the organic matter being controlled in relation to the analysed content of said organic fatty acid.

4. The method according to claim 3, wherein the addition of cobalt is controlled to provide a concentration of palmitic acid in the sludge of less than 1500 mg/l.

5. The method according to claim 1, wherein the amount of iron added corresponds to an addition of at least 500 g of Fe added per $m^3$ of substrate fed to the reactor.

6. The method according to claim 1, wherein the amount of hydrochloric acid added corresponds to an addition of at least 10 g HCl added per $m^3$ of substrate fed to the reactor.

7. The method according to claim 2, wherein, on a regular basis, a sample of the digested sludge is taken out of the reactor and is analysed for the content of at least one organic fatty acid having more than 10 carbon atoms, the amount of cobalt added to the organic matter being controlled in relation to the analysed content of said organic fatty acid.

8. The method according to claim 7, wherein the addition of cobalt is controlled to provide a concentration of palmitic acid in the sludge of less than 1500 mg/l.

* * * * *

UNITED STATES PATENT AND TRADEMARK OFFICE
CERTIFICATE OF CORRECTION

PATENT NO. : 7,622,286 B2 Page 1 of 1
APPLICATION NO. : 11/604828
DATED : November 24, 2009
INVENTOR(S) : Jörgen Ejlertsson It is certified that error appears in the above-identified patent and that said Letters Patent is hereby corrected as shown below:

Title Page, Item (73) Assignee should read:

--Assignee: Tekniska Verken i Linköping AB,
Linköping AB (SE)--

Item (56) References Cited The Swedish Foreign Patent Document should read:

--SE     525 313     2/2005--

Signed and Sealed this

Twenty-third Day of March, 2010

David J. Kappos
*Director of the United States Patent and Trademark Office*